United States Patent [19]

Pivette et al.

[11] 3,997,354
[45] Dec. 14, 1976

[54] BITUMINOUS BINDER COMPOSITIONS

[75] Inventors: Pierre Pivette, Sucy-en-Brie; Philippe Häicour, Paris, both of France

[73] Assignee: Pierrefitte-Auby, Paris, France

[22] Filed: Jan. 29, 1975

[21] Appl. No.: 545,224

[30] Foreign Application Priority Data

Jan. 31, 1974  France ............... 74.03161

[52] U.S. Cl. .................... 106/273 N; 106/277; 106/278; 106/279; 106/281 N; 252/311.5; 252/357

[51] Int. Cl.² ............... C08J 3/00; C08K 5/17; C08K 5/34; C08L 95/00

[58] Field of Search ............. 106/273, 273 N, 281, 106/277, 278, 279; 260/256.4 R, 256.4 B, 256.4 N, 404.5, 251 R; 252/357

[56] References Cited

UNITED STATES PATENTS

| 2,438,318 | 3/1948 | Johnson ............ 106/281 N |
| 2,534,828 | 12/1950 | Mitchell et al. ............ 106/273 N |
| 2,640,029 | 5/1953 | Blair, Jr. et al. ............ 252/8.55 |
| 2,658,895 | 11/1953 | Ballard et al. ............ 106/273 N X |
| 2,713,559 | 7/1955 | Smith ............ 260/251 R X |
| 2,736,658 | 2/1956 | Pfohl et al. ............ 260/404.5 AA |
| 3,895,172 | 7/1975 | Jones ............ 106/277 |

FOREIGN PATENTS OR APPLICATIONS 659,884  10/1951  United Kingdom ........... 106/273 N

*Primary Examiner*—Joan E. Welcome
*Attorney, Agent, or Firm*—Fleit & Jacobson

[57] ABSTRACT

The invention relates to bituminous binder compositions containing in the proportion of 0.5 to 2% by weight of the bitumen used, a mixture of polynitrogenous compounds such as those obtained by reacting polyalkylene polyamines having the general structure: $R-NH(CH_2-CH_2-CH_2-NH)_n-H$ with formic acid while removing the reaction water. The main component consists of a tetrahydropyrimidine substituted on nitrogen by means of a long linear chain comprising one or a plurality of amine groups having the general structure:

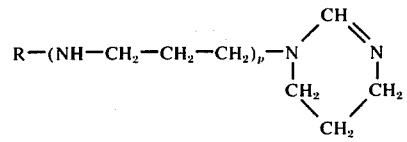

wherein R is a saturated or unsaturated linear hydrocarbon comprising 8 to 22 carbon atoms, $n$ is an integer from 2 to 5 and $p$ another integer equal to $(n-1)$, that is from 1 to 4.

5 Claims, No Drawings

BITUMINOUS BINDER COMPOSITIONS

The present invention is concerned with improvements in or relating to bituminous binder compositions and emulsions, obtained by using substances capable of increasing the adhesiveness between bitumens and mineral aggregates used notably in the road-surfacing industry.

As a rule, in this specific field fatty-chain linear amines and polyamines, or more or less cyclicized condensates of fatty acids with polyethylene polyamines or polypropylene polyamines, are used.

Now the applicants have found that when in the same molecule amine groups attached directly to the fatty chain and not included in a cycle are associated with cyclicized nitrogenous structures, the resultant products have very satisfactory doping and emulsifying properties with respect to fatty-chain linear polyamines, said products, like the cyclic condensates of fatty acids and polyamines, preserving their properties when heated, even during a relatively extended time period, within the bituminous mass. However, in addition these products, obtainable through a simple process from fatty-chain polyalkylene polyamines, are advantageous in comparison with these last-mentioned polyamines in that their melting point is definitely lower, the difference being in certain cases as great as 20° C, so that the handling of these products is greatly facilitated since, more specifically, they can be cast and pumped at lower temperatures.

The products utilized for carrying out the present invention may be obtained from polyalkylene polyamines having the general structure:

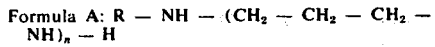

wherein R is a saturated or unsaturated linear hydrocarbon chain comprising 8 to 22 carbon atoms, and $n$ is an integer within the range of 2 to 5. These polyamines are themselves prepared from corresponding monoamines by successive cyanoethylations and hydrogenations, by heating said polyamines with a suitable amount of formic acid and gradually removing the reaction water.

The amount of formic acid used varies as a function of the average molar mass of the initial polyamine. As a rule, one formic acid equivalent per primary amine equivalent is used. However, it would not constitute a departure from the present invention to use products obtained by using different proportions of formic acid, but it should be born in mind that increasing the formic acid to amine ratio leads to an increment in the substituted-formamide groups, and that reducing said ratio leads to a reduction in the cyclization rate.

The amounts of formic acid used may vary from 1/12th to 1/5th by weight of the initial polyamine amount. The removal of the reaction water is facilitated when the reaction is carried out under reduced pressure or if an azeotropic distillation is effected by using a suitable solvent.

The resultant products utilized according to the present invention are complex mixtures of compounds comprising unmodified amine groups, formamide-substituted groups and elements having a cyclic amidine structure of the tetrahydropyrimidine type obtained on the one hand from the terminal primary amine group of the nearest secondary amine, and on the other hand from the formic acid carboxylic group. The main component element of these complex mixtures is a nitrogen substituted tetrahydropyrimidine, the substituent consisting of a long linear chain comprising one or more amine groups.

The structure of this compound may be represented diagrammatically as follows:

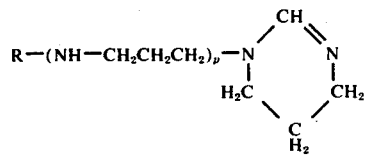

wherein R is the alkyl chain of the initial polyamine and $p$ an integer equal to $(n - 1)$, therefore within the range of 1 to 4.

The relative proportions of these various functional groups may be determined as follows:

The amide groups and the cyclic formamidine structures may be easily determined by infrared spectrophotometry. In this case, from the very beginning of the reaction an intense vibration located at about 1670 cm$^{-1}$ appears, this vibration corresponding to the amide groups. The intensity of this vibration decreases gradually as the reaction progresses, while another vibration characteristic of the formamidine groups of the tetrahydropyridine cycles appears (and increases) at about 1620 cm$^{-1}$.

A first, rough estimation of the amide group content and of the tetrahydropyrimidine cycle content can be obtained by a mere examination of the infrared spectrum of the modified polyamines. Furthermore, a chemical analysis will give with greater precision the relative proportions of the various chemical forms assumed during the reaction by the aminated nitrogen of the initial polyamines. In fact, by using potentiometric methods, it is possible to proportion separately the amine groups on the one hand and the amide groups on the other hand, the amide groups displaying during the analysis a considerably weaker basicity than the amine groups. On the other hand, one of the two nitrogen atoms of the heterocyclic structures displays no basic character whatsoever in the analysis. The non-basic nitrogen content may therefore be calculated from the difference between the total nitrogen and the sum of the aminated nitrogen and of the amide nitrogen.

The relative proportions of these various component elements vary of course as a function of the specific nature of the initial polyamine and also of the quantity of formic acid implemented. The modified polyamines according to this invention contain as a rule 7 to 14 per cent of total nitrogen, 3.5 to 11.9% of aminated nitrogen incorporated in a linear hydrocarbon chain or in a heterocycle of the tetrahydropyrimidine type, 0.35 to 3.5% of amide nitrogen and 0.35 to 6.3% of non-basic cyclic nitrogen.

The products utilized for carrying out the present invention are generally either mixed directly with the bituminous binders or utilized for emulsifying bitumen according to the conventional methods applied in the preparation of bitumen emulsions. Other modes of application known in actual practice also fall within the scope of this invention. Among these modes of application are a preliminary treatment of the granular material or aggregates with aqueous or oily solutions or dispersions of the products of this invention before coating the former with the hydrocarbon binders; spraying the solutions of products of this invention directly into the mixers when coating said granular materials or aggregates, and preparing additives for modifying emulsions obtained according to conventional formulae.

The proportions may vary according to the specific means contemplated for utilizing the doping product of this invention and to the nature and specific surface condition of the materials to be coated. Generally, these proportions range from 0.05 to 2% by weight of the binder. Lower percentages cannot be attained due to the difficulty of achieving an accurate proportioning. Above these limits, the gain in efficiency does not justify as a rule the increased cost.

The following Examples illustrate, without limiting the present invention, the means implemented for obtaining the products utilized within the scope of this invention, as well as their physical and chemical properties, and their efficiency.

EXAMPLE 1

990g of a product known under the Trade Name "TRINORAM S" and manufactured by Pierrefitte-Auby of France, of which the main component is a tallow triamine (corresponding to Formula A) having a melting point of about 35° C, are melted at about 50° C. Then 137 g of 98% formic acid are added during half an hour. The temperature rises to 125° C and this temperature is maintained for 1 hour. The temperature is subsequently raised to 150°–155° C and kept at this level for 90 minutes. A 25-mm Hg vacuum is then applied gradually and the temperature is further raised to 220° C. These conditions are then maintained during 2½ hours. During this operation, about 100 g of distillate are removed to yield, on the other hand, 920 g of product having a melting point of 13° C.

The main component of the doping product thus obtained is a tetrahydropyrimidine corresponding to Formula B hereinabove, wherein $p = 1$ and R is an alkyl chain due to the use of tallow.

The infrared spectrum of this product has the characteristic appearance of the modified polyamines according to this invention. The analysis gave the following results:
Total nitrogen = 10.1% Aminated nitrogen = 5.74% Amido nitrogen = 1.75%.

This doping product was tested for its efficiency as a doping medium for improving the adhesiveness of bitumen on road-surface aggregates in comparison with the initial triamine. The results of these tests evidence the preservation and even, under certain conditions, the improvement of the doping properties, with the advantage that the product obtained according to the teachings of this invention is in the liquid state at a relatively low temperature.

Conventionally, adhesiveness is measured by means of a coating test followed by a stripping test in which hot water is used (actually, boiling water was used during the above-disclosed tests).

A siliceous granular material (quartzite) having a granulometry of 10/12.5 mm was coated at a relatively low temperature (about 110° C) with 10% of fluidifed bitumen (150 to 250 seconds B.R.T.) to which the doping product of this invention had been added. After cooling, the coated material was immersed in water and the material then heated to boiling temperature of water and kept thereat for 10 minutes. The adhesiveness is expressed by estimating the relative surface area of the granular material which remains covered with a relatively thick layer of binder.

The following adhesiveness Table illustrates the doping efficiency of the product according to this Example in comparison with Trinoram S from which it is derived:

| Dope content | Trinoram S | Product of Example 1 |
|---|---|---|
| 0.3% | 75% | 90% |
| 0.5% | 90% | 100% |

The thermal resistance of the product according to Example 1 was also tested by enclosing a bitumen doped in the proportion of 10 kg per ton of binder in tightly closed and sealed containers, and exposing said containers during 3 days at the following temperatures: room, 160° and 200° C. The following comparative residual adhesiveness results prove the exceptional thermal resistance imparted by the product of this invention.

| 3 days at room temperature | 3 days at 160° C | 3 days at 200° C |
|---|---|---|
| 90% | 90% | slightly below 100% |

EXAMPLE 2

In a modified embodiment of the process described in the preceding Example, the temperature raising conditions were modified.

235 g of 98% formic acid are added while stirring to 1650 g of tallow triamine (Trinoram S), a product manufactured by Pierrefitte-Auby. The temperature rises to 110° C. Then the temperature is raised to 125° C and kept at this level for 1 hour. The temperature is subsequently raised gradually in 2 hours to 220° C while gradually setting a vacuum such as to obtain a residual pressure of 25 mm Hg. This temperature and this vacuum are maintained for 2 hours. Thus, 1620 g of a product having a melting point below 14° C are obtained.

The infrared spectrum of the product thus obtained has the characteristic appearance of the modified polyamines according to this invention. The analysis gave the following results:
Total nitrogen = 10.07%
Aminated nitrogen = 6.16%
Amido-nitrogen = 1.48%.

The product obtained in this Example was utilized as an emulsifier in the following test:

By way of example, a road bitumen of standard quality (penetration rate = 180 to 220 tenths of mm at 25° C) was emulsified by means of an ATOMIX turbomixer under conventional temperature conditions (binder at 145° C, aqueous phase at 55° C), to adhere to the global formula:

| | |
|---|---|
| Bitumen | 600 kg |
| Emulsifier | 2 kg |
| HCl, Q.s.p. pH | 1.8 to 2 |

-continued

| | |
|---|---|
| Water q.s.p. | 1000 kg. |

The emulsion thus obtained from the product of this Example is compared with the conventional emulsion obtained from the well-known product sold under the Trade Name Dinoram S and manufactured by Pierrefitte-Auby, which consists of a tallow propylene diamine, according to Formula A.

| Properties of the emulsion | with Dinoram S | with product of this Example |
|---|---|---|
| Engler viscosity at 25° C | 3.9 | 4.4 |
| Particles retained in a 0.63-mm mesh screen | nil | nil |
| Breaking time on quartzite | 20 mn | 10 mn |
| Breaking time on limestone | 20 mn | 7 mn |
| Breaking index according to the French Laboratoire Central des Ponts et Chaussees | 158 | 123 |
| Adhesiveness on quartz | 50% | 90% |
| Adhesiveness on limestone | 50% | 75% |

EXAMPLE 3

From a product marketed by Pierrefitte-Auby under the Trade Name "Polyram S" (a tetramine corresponding to formula A) and having as a main component a tallow tetramine (m.p. approximating 40° C), and by applying a process similar to that described in Example 1 hereinabove, a product having a m.p. below 15° C was obtained.

The main component of the resultant product is a tetrahydropyrimidine corresponding to the above Formula B, wherein $p = 2$ and R is an alkyl chain derived from tallow.

The infrared spectrum of the product thus obtained had the characteristic appearance of polyamines modified according to this invention. The analysis gave the following results:

Total nitrogen = 11.55%
Aminated nitrogen = 5.75%
Amido nitrogen = 1.57%.

This product was tested under the same conditions as in the preceding Examples 1 and 2, and displayed the same efficiency, as an adhesiveness dope, as the products of said Examples 1 and 2.

EXAMPLE 4

990 g of tallow triamine (Trinoram S) are dissolved at 60° C in 400 g of xylene. Then 93 g of 98% formic acid are added, and the mix is subsequently distilled to remove water while recycling continuously the xylene, the latter separating by decantation. During this step, the mix temperature is maintained at about 150° C. When the removal of water decreases, one fraction of the xylene is distilled off until the b.p. of the mixture is about 210° C and the operation is continued while recycling the decanted xylene until the removal of water ceases. Then, the residual xylene is evaporated in vacuo. Thus, 939 g of a product titrating 10, 12% of total nitrogen, 7% of aminated nitrogen and 2.42% of amido-nitrogen are obtained. This product, when tested as an adhesiveness dope under the same conditions as in Examples 1 and 2, displayed a comparable efficiency.

What is claimed as new is:

1. A bituminous binder composition comprising a bituminous substance and 0.05 to 2 % by weight of a mixture of polynitrogenous compounds obtained by reacting polyalkylene polyamines having the general structure:

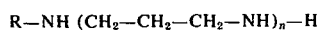

R—NH (CH$_2$—CH$_2$—CH$_2$—NH)$_n$—H with formic acid while removing the reaction water, said mixture of polynitrogenous compounds having as the main component a tetrahydropyrimidine substituted on a nitrogen by a long linear chain comprising one or more amine groups having the general structure:

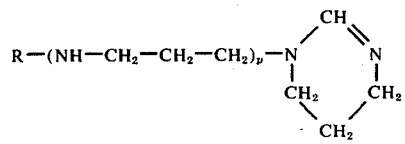

wherein R is a saturated or unsaturated linear hydrocarbon comprising 8 to 22 carbon atoms, $n$ is an integer from 2 to 5 and $p$ is an integer equal to $(n-1)$.

2. A composition as set forth in claim 1, wherein $p$ is 1 and R is an alkyl chain derived from tallow.

3. A composition as set forth in claim 1, wherein $p$ is 2 and R is an alkyl chain derived from tallow.

4. A bituminous binder composition comprising a bituminous substance and 0.05 to 2% by weight of a mixture of polynitrogenous compounds obtained by reacting polyalkylene polyamines having the general structure:

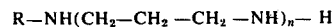

R—NH(CH$_2$—CH$_2$ —CH$_2$ —NH)$_n$— H with formic acid while removing the reaction water, said mixture of polynitrogenous compounds having as the main component a tetrahydropyrimidine having a cyclic amidine structure substituted on a nitrogen by a long linear chain having the general structure:

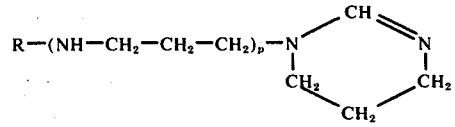

wherein R is a saturated or unsaturated linear hydrocarbon comprising 8 to 22 carbon atoms, $n$ is an integer from 2 to 5 and $p$ is an integer equal to $(n-1)$, the other components of said mixture of polynitrogenous compounds including unmodified amine groups and formamide substituted groups, said mixture of polynitrogenous compounds having a melting point not higher than 15° C.

5. A composition as set forth in claim 4, wherein the proportion of amido-nitrogen is between 0.35 and 3.5 % based on the total product.

* * * * *